(12) United States Patent
Richter

(10) Patent No.: US 6,315,794 B1
(45) Date of Patent: Nov. 13, 2001

(54) MULTILAYERED METAL STENT

(75) Inventor: Jacob Richter, Ramat Hasharon (IL)

(73) Assignee: Medinol Ltd., Tel Aviv (IL)

( * ) Notice: Subject to any disclaimer, the term of this patent is extended or adjusted under 35 U.S.C. 154(b) by 0 days.

(21) Appl. No.: 09/335,599

(22) Filed: Jun. 18, 1999

Related U.S. Application Data

(63) Continuation of application No. 08/969,576, filed on Nov. 13, 1997, now abandoned.

(51) Int. Cl.[7] .................................................. A61F 2/00
(52) U.S. Cl. ........................................ 623/1.34; 623/1.46
(58) Field of Search ................................. 623/1.13, 1.34, 623/1.46

(56) References Cited

U.S. PATENT DOCUMENTS

| | | | |
|---|---|---|---|
| 4,768,507 | 9/1988 | Fischell et al. | 128/303 |
| 4,776,337 | 10/1988 | Palmaz | 623/1 |
| 4,886,062 | 12/1989 | Wiktor | 128/343 |
| 4,994,071 | 2/1991 | MacGregory | 606/194 |
| 5,024,232 | 6/1991 | Smid et al. | 128/654 |
| 5,176,617 | 1/1993 | Fischell et al. | 600/3 |
| 5,201,901 | 4/1993 | Harada et al. | 606/198 |
| 5,207,706 | 5/1993 | Menaker | 623/1 |
| 5,344,425 | 9/1994 | Sawyer | 606/198 |
| 5,464,438 | 11/1995 | Meanker | 623/1 |
| 5,607,442 | 3/1997 | Fischell et al. | 606/191 |
| 5,628,790 | 5/1997 | Davidson et al. | 623/2 |
| 5,630,840 | 5/1997 | Mayer | 623/1 |
| 5,632,779 | 5/1997 | Davidson | 623/12 |
| 5,636,641 | 6/1997 | Fariabi | 128/772 |
| 5,647,858 | 7/1997 | Davidson | 604/264 |
| 5,649,951 | 7/1997 | Davidson | 606/198 |
| 5,649,977 | 7/1997 | Campbell | 623/1 |
| 5,725,572 | 3/1998 | Lam | 623/1 |
| 5,800,511 | * 9/1998 | Mayer | 623/1.1 |
| 5,824,045 | 10/1998 | Alt | 623/1 |
| 5,858,556 | * 1/1999 | Eckert | 623/1.1 |
| 6,174,329 | * 1/2001 | Callol | 623/1.34 |

FOREIGN PATENT DOCUMENTS

| | | | |
|---|---|---|---|
| 29701758 | 5/1997 | (DE) . | |
| 0709068 | 5/1996 | (EP) . | |
| 0 824 900 | 2/1998 | (EP) . | |
| 0 679 372 A2 | 11/1995 | (EP) | A61B/19/00 |
| 93/19804 | 10/1993 | (WO) . | |
| 95/21592 | 8/1995 | (WO) . | |
| 96/34580 | 11/1996 | (WO) . | |
| 99/02195 | 1/1999 | (WO) . | |
| WO 96/03092A1 | 2/1996 | (WO) | A61F/2/02 |
| WO 96/25960 | 8/1996 | (WO) | A61L/27/00 |

* cited by examiner

Primary Examiner—Michael J. Milano
(74) Attorney, Agent, or Firm—Kenyon & Kenyon

(57) ABSTRACT

Coated stents for increased radiopacity. In one embodiment, the present invention includes a stent in the form of a tubular member comprising struts of a first material, and a first coating on the tubular member. The first coating substantially covers the tubular member and is substantially uniform in thickness. The first coating comprises a second material that is more radiopaque than the first material. In another embodiment, the stent further comprises a second coating between the tubular member and the first coating, wherein the second coating covers only a portion of the tubular member. In yet another embodiment, the stent is a coated bifurcated stent for positioning in a bifurcated body lumen.

13 Claims, 5 Drawing Sheets

MULTILAYERED METAL STENT

This application is a Continuation of Ser. No. 08/969,576, filed Nov. 13,1997 now abandoned.

FIELD OF THE INVENTION

The present invention relates to stents for deploying within body lumens, and more particularly, to optimizing the radiopacity of such stents.

BACKGROUND

Stents are tubular structures that are implanted inside bodily conduits, blood vessels or other body lumens to widen and/or to help keep such lumens open. Typically, stents are delivered into the body while in a compressed configuration, and are thereafter expanded to a final diameter once positioned at a target location within the lumen. Stents are often used following or substituting for balloon angioplasty to repair stenosis and to prevent future restenosis and, more generally, may be used in repairing any of a number of tubular body conduits such as those in the vascular, biliary, genitourinary, gastrointestinal, respiratory and other systems. Exemplary patents in the field of stents formed of wire, for example, include U.S. Pat. Nos. 5,019,090 to Pichuk; U.S. Pat. No. 5,161,547 to Tower; U.S. Pat. No. 4,950,227 to Savin et al.; U.S. Pat. No. 5,314,472 to Fontaine; U.S. Pat. Nos. 4,886,062 and 4,969,458 to Wiktor; and U.S. Pat. No. 4,856,516 to Hillstead; each of which is incorporated herein by reference. Stents formed of cut stock metal, for example, are described in U.S. Pat. No. 4,733,665 to Palmaz; U.S. Pat. No. 4,762,128 to Rosenbluth; U.S. Pat. No. 5,102,417 to Palmaz and Schatz; U.S. Pat. No. 5,195,984 to Schatz; WO 91 FR013820 to Meadox; and WO 96 03092 to Medinol, each of which is incorporated herein by reference. Bifurcating stents are described in U.S. Pat. No. 4,994,071 to MacGregor, and commonly-assigned U.S. patent application Ser. No. 08/642,297, filed May 3, 1996, each of which is incorporated herein by reference.

For stents to be effective, it is essential that they be accurately positioned at a target location within a desired body lumen. This is especially true where, for example, multiple stenting is required with overlapping stents to cover excessively long regions or bifurcating vessels. In these and other cases, it is often necessary to visually observe the stent both during placement in the body and after expansion of the stent. Various approaches have been attempted to achieve such visualization. For example, stents have been made from radiopaque (i.e., not allowing the passage of x-rays, gamma rays, or other forms of radiant energy) metals, such as tantalum and platinum, to facilitate fluoroscopic techniques. One of the potential problems with such stents, however, is that a useful balance of radiopacity and stent strength is difficult, if not impossible, to achieve. For example, in order to form such a stent of adequate strength, it is often necessary to increase stent dimensions such that the stent becomes overly radiopaque. Consequently, fluoroscopy of such a stent after deployment can hide the angiographic details of the vessel in which it is implanted, thus making it difficult to assess problems such as tissue prolapse and hyperplasia.

Another technique that has been used to achieve the visualization of stents is the joining of radiopaque markers to stents at predetermined locations. The joining of the stent and marker materials (e.g., stainless steel and gold, respectively), however, can create a junction potential or turbulence in blood and thus promote thrombotic events, such as clotting. Consequently, the size of the markers is minimized to avoid this problem, with the adverse effect of greatly decreasing fluoroscopic visibility and rendering such visibility orientation-sensitive.

Yet another technique that has been used to achieve the visualization of stents is to simply increase the thickness of such stents to thereby increase radiopacity. Overly thick stent struts, however, effectively create an obstruction to blood flow. In addition, design limitations for stents having thick struts often result in large gaps between these struts, thus decreasing the support of a surrounding lumen. Furthermore, overly thick stent struts could adversely affect stent flexibility.

There is thus a need for the increased radiopacity of stents without sacrificing stent mechanical properties or performance. The coating of stents with radiopaque materials is described in U.S. Pat. No. 5,607,442 to Fishell et al. According to this patent, the disclosed radiopaque coating is much thicker on longitudinal stent members when compared with radial stent members such that only the longitudinal stent members are visible during fluoroscopy.

SUMMARY OF THE INVENTION

The present invention provides stents of optimized radiopacity and mechanical properties.

In one embodiment, the present invention includes a stent comprising a tubular member which comprises struts of a first material, and a first coating on the tubular member. The first coating substantially covers the tubular member and is substantially uniform in thickness. The first coating comprises a second material that is more radiopaque than the first material comprising the struts.

In another embodiment of the present invention, the stent further comprises a second coating disposed between the tubular member and the first coating, wherein the second coating covers only a portion of the tubular member. When the stent is observed with fluoroscopy, the portion where the second coating exists appears darker than where only the first coating exists.

In yet another embodiment of the present invention, the stent is a coated bifurcated stent for positioning in a body lumen that is bifurcated into a trunk lumen and a branch lumen. The stent has trunk and branch legs for positioning in trunk and branch lumens, respectively. In this embodiment, the stent is coated with multiple layers of radiopaque materials such when the stent is observed with fluoroscopy, the branch leg appears darker than the trunk leg.

DETAILED DESCRIPTION

The present invention provides optimal radiopacity of stents without sacrificing mechanical properties or performance. A stent according to the present invention is made from a base material having desired mechanical properties (e.g., strength) and coated with a material to provide optimal, radiopacity to the stent. The radiopacity of the stents of the present invention is optimized in the sense that, during fluoroscopic procedures, the stents are entirely visible but are not so radiopaque that angiographic details are masked. The present invention thus provides for stents that have both the desired mechanical properties of the base material and the desired radiopacity of the coating material. The stents of the present invention have the additional benefit of being manufactured according to simple and reproducible techniques.

Figure 1A:
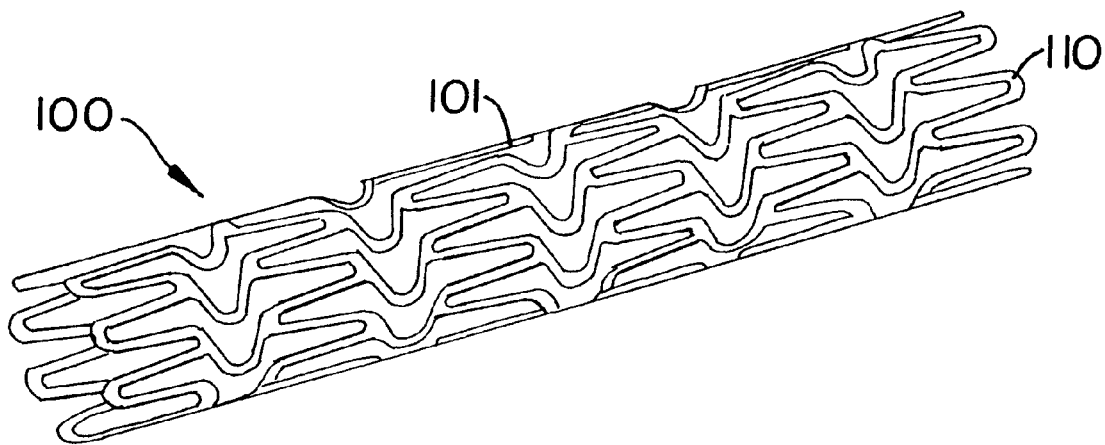
FIG. 1A illustrates a coated patterned stent, in accordance with an embodiment of the present invention.
Figure 1B:
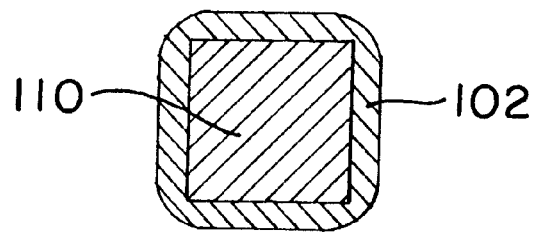
FIG. 1B is a cross-sectional view of a typical strut from the stent of FIG. 1A.

In one embodiment of the present invention, stent 100 is a tubular member 101 comprising struts 110 as shown in FIGS. 1A–1B. The term "strut", as used herein, is intended to mean any structural member of a stent, such as any radial, longitudinal, or other members made from wire, cut stock, or other materials. Struts 110 comprise a first material that is selected for its mechanical properties such as, for example, the ability to be delivered into the body while in a compressed configuration, the ability to expand or be expanded once positioned to a target location, the ability to resist recoil, and the ability to hold open a body lumen during the stent lifetime. Typical exemplary materials for struts 110 include stainless steel and nitinol. Stent 100 further comprises a first coating 102 of a second material that is selected for its radiopacity. Coating 102 covers the entire tubular member 101 with the result that intersections of the first and second materials are not exposed to the exterior of the stent. By not exposing intersections of the first and second materials to the exterior of the stent, the risks of creating a junction potential in the blood and causing the electrolytic corrosion of the stent are precluded. FIG. 1B shows a cross-sectional view of coating 102 on a typical strut 110 of stent 100. Although FIG. 1B shows both the strut 110 and coating 102 to be substantially square in cross-sectional shape, the actual cross-sectional shape of either or both of these elements is any desired or suitable shape, such as circular, oval-shaped, rectangular, or any of a number of irregular shapes.

Coating 102 is applied to tubular member 101 according to any suitable technique such as, for example, electroplating, electroless plating, ion beam aided deposition, physical vapor deposition, chemical vapor deposition, electron beam evaporation, hot-dipping or any other suitable sputtering or evaporation process. Coating 102 comprises any suitable radiopaque material such as, for example, gold, platinum, silver and tantalum.

The thickness of coating 102 is an important aspect of the present invention. A coating that is too thick will result in a stent that is overly radiopaque, and angiographic details will consequently be masked during subsequent fluoroscopy. In addition, stent rigidity often increases with coating thickness, thus making it difficult to expand the stent for placement in a body lumen if the coating is too thick. On the other hand, a radiopaque coating that is too thin will not be adequately visible during fluoroscopy. Depending on the material and configuration of the tubular member 101, and the material of the coating 102, the thickness of coating 102 is optimized to provide the optimum balance between radiopacity and strength. In general, however, it is preferred that coating 102 be approximately 1–20%, and more preferably approximately 5–15%, of the underlying strut thickness. In all embodiments of the present invention, coating 102 is applied to the entire stent such that it is wholly visible during fluoroscopy. Accordingly, any suboptimal expansion at any position along the stent is visible and any deviations from perfect circular expansion can be noticed.

Figure 2A:
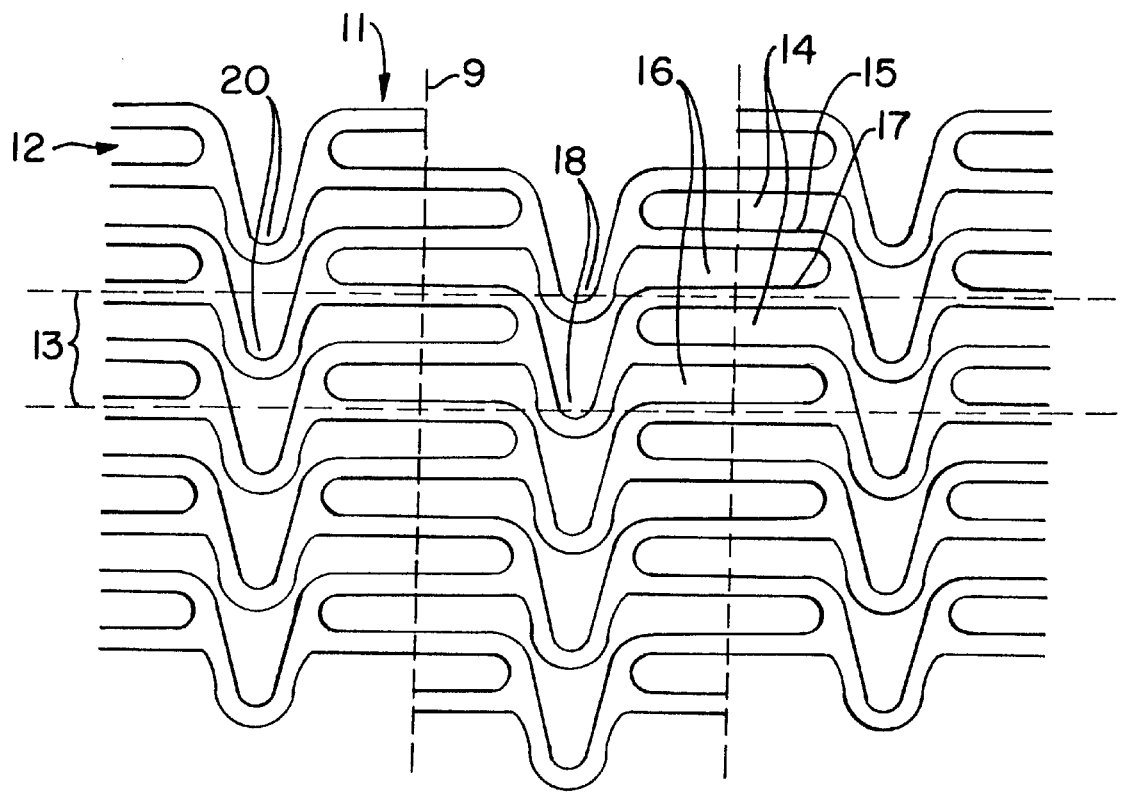
FIG. 2A illustrates a preferred stent configuration in an embodiment of the present invention.
Figure 2B:
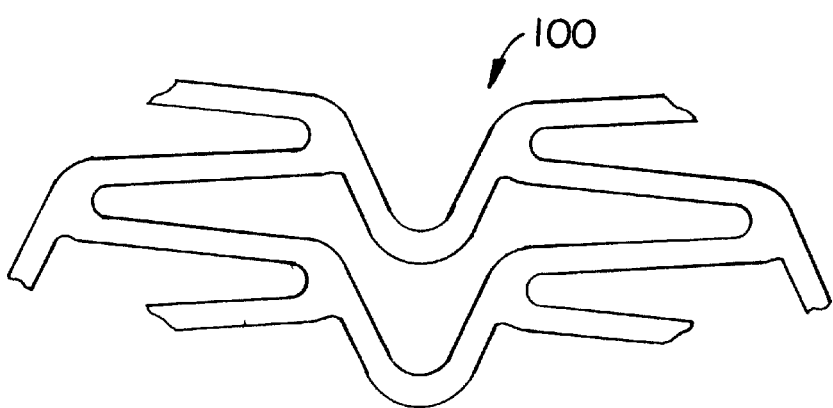
FIG. 2B illustrates a most preferred configuration for a single stent cell, in accordance with an embodiment of the present invention.

The stents of the present invention are of any suitable configuration, although the patterned configurations as described in WO 96 03092 and commonly-assigned, allowed U.S. patent application Ser. No. 08/457,354, filed May 31, 1995 and incorporated herein by reference, are preferred for all embodiments of the present invention. As an example of such a configuration (a close-up of which is shown in FIGS. 2A and 2B), stent 100 is a tube having sides that are formed into a plurality of two orthogonal meander patterns intertwined with each other. The term "meander pattern" is used herein to describe a periodic pattern about a center line and "orthogonal meander patterns" are patterns having center lines that are orthogonal to each other.

As shown in FIG. 2A, stent 100 optionally includes two meander patterns 11 and 12. Meander pattern 11 is a vertical sinusoid having a vertical center line 9. Meander pattern 11 has two loops 14 and 16 per period wherein loops 14 open to the right while loops 16 open to the left. Loops 14 and 16 share common members 15 and 17, where member 15 connects from one loop 14 to its following loop 16 and member 17 connects from one loop 16 to its following loop 14. Meander pattern 12 is a horizontal pattern having a horizontal center line 13. Meander pattern 12 also has loops, labeled 18 and 20, which may be oriented in the same or opposite directions. The stent configuration shown in FIG. 2A, with orthogonal meander patterns 11 and 12, provides for a high degree of stent flexibility to facilitate expansion, yet results in a high degree of rigidity once the stent is expanded. FIG. 2B illustrates a detailed view of a single cell of the most preferred stent configuration of the present invention.

Figure 3A:
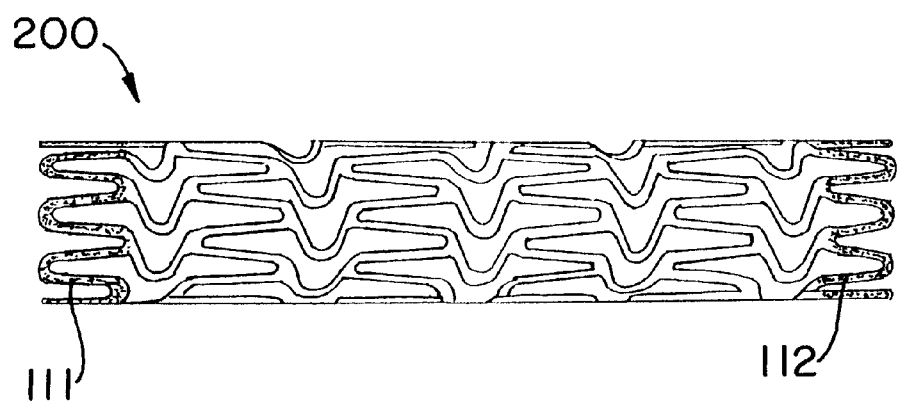
FIG. 3A illustrates a patterned stent having multiple coatings thereon, in accordance with an embodiment of the present invention.
Figure 3B:
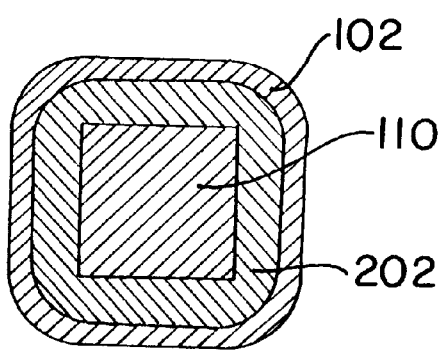
FIG. 3B is a cross-sectional view of a typical strut from the stent of FIG. 3A, at a location where two coatings have been applied to the stent.
Figure 3C:
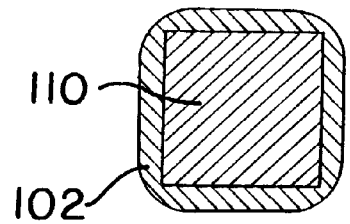
FIG. 3C is a cross-sectional view of a typical strut from the stent of FIG. 3A, at a location where only one coating has been applied to the stent.

In another embodiment of the invention as shown in FIGS. 3A–3C, stent 200 includes a second coating 202 applied between the struts 110 of stent 200 and first coating 102. In distinction to first coating 102, however, second coating 202 covers only a portion or multiple portions of stent 200 so that isolated regions of stent 200 are most visible during fluoroscopy. For example, second coating 202 is applied to one or both of the proximate 111 and distal 112 ends of stent 100, as shown in FIG. 3A. As in the embodiment shown in FIGS. 1A–1B, however, first coating 102 covers the entire stent 200 shown in FIGS. 3A–3C. FIGS. 3B and 3C show cross-sectional views of struts 110 of stent 100 where second coating 202 has and has not been applied, respectively. Such isolated marking is useful for the accurate positioning of the ends of stents, such as, for example, in the case of multiple stenting wherein the overlapping length is important, or, for example, in the case of ostial stenting wherein the position of the stent end relative to the ostium is important.

Second coating 202 comprises a suitable radiopaque material such as gold, platinum, silver and tantalum, and may be the same or different material as first coating 102.

Second coating 202 is applied to stent 200 by any suitable technique, such as those described for the application of first coating 102. Second coating 202 is applied only to a portion or multiple portions of tubular member 101, for example, by masking during the application of second coating 202 or by isolated etching after second coating 202 is applied. It is to be appreciated that although coating 202 is herein described to be a "second" coating, it is applied to stent 200 before the application of first coating 102.

When used, second coating 202 has a thickness that will result in increased radiopacity at the portion(s) where second coating 202 exists when compared with the portion(s) where second coating 202 does not exist. Because second coating 202 is applied to only a portion or multiple portions of stent 200, it can be thickly applied without significantly affecting the resistance of stent 200 to expand or affecting the visibility of arterial details during fluoroscopy. Like first coating 102, the thickness of second coating 202 is optimized to provide a desired balance between stent radiopacity and other properties. In general, however, second coating 202 is typically as thick or thicker than first coating 102. When both first and second coatings 102, 202 are applied, it is generally preferred that the thickness of first and second coatings 102, 202 are about 1–5% and 5–15%, respectively, of the underlying stent strut thickness. Furthermore, the combined thickness of first and second coatings 102, 202 typically does not exceed 25% of the underlying stent strut thickness. As an illustrative example, second coating 202 is applied to a thickness of about 10 microns onto a stent having 100 micron diameter struts. First coating 102 is then applied to a thickness of about 1 micron.

Figure 4A:
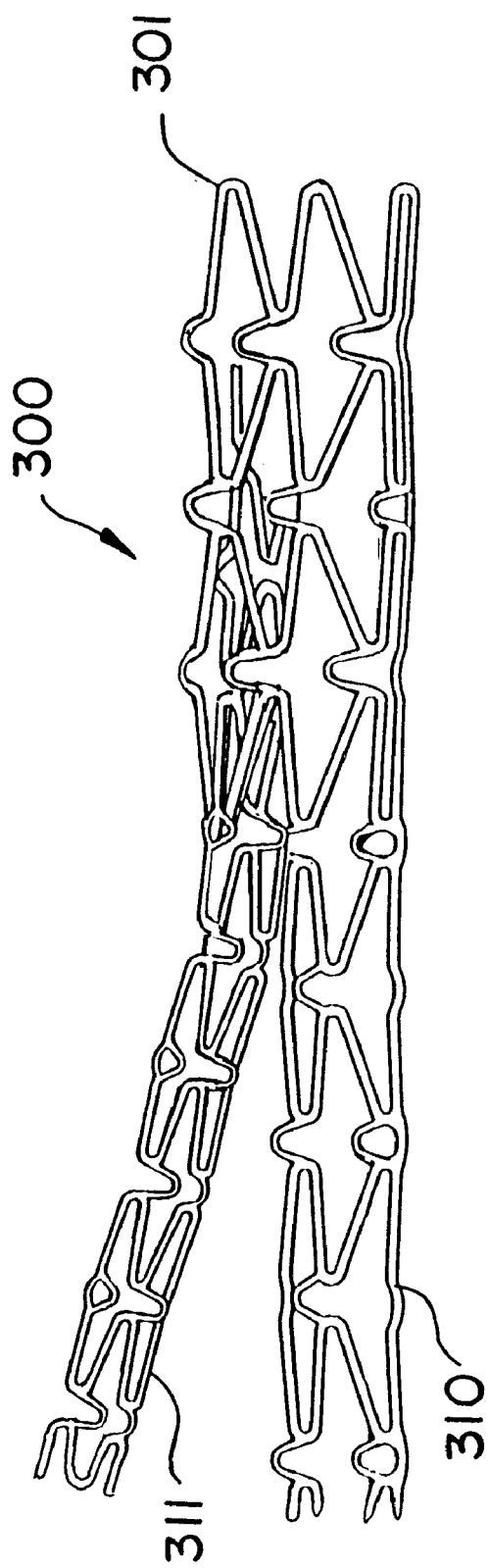
FIG. 4A illustrates a first coated bifurcated stent, in accordance with an embodiment of the present invention.

In another embodiment of the present invention, stent 300 is a bifurcated stent as shown in FIG. 4A. Stent 300 comprises a tubular member 301 that is bifurcated into tubular trunk and branch legs 310, 311 for positioning in trunk and branch lumens of a bifurcated lumen, respectively. In this embodiment, the entire stent is coated with first coating 102 as described for the embodiments shown in FIGS. 1 and 3. Branch leg 311, however, includes second coating 202 disposed between tubular member 301 and first coating 102 such that when stent 300 is observed with fluoroscopy, branch leg 311 appears darker than the trunk leg 310. The cross-sectional views of the struts of stent 300 thus appear as shown in FIGS. 3B and 3C for branch and trunk legs 311, 310, respectively. Such a configuration is useful for aligning and inserting branch leg 311 into a branch lumen.

Figure 4B:
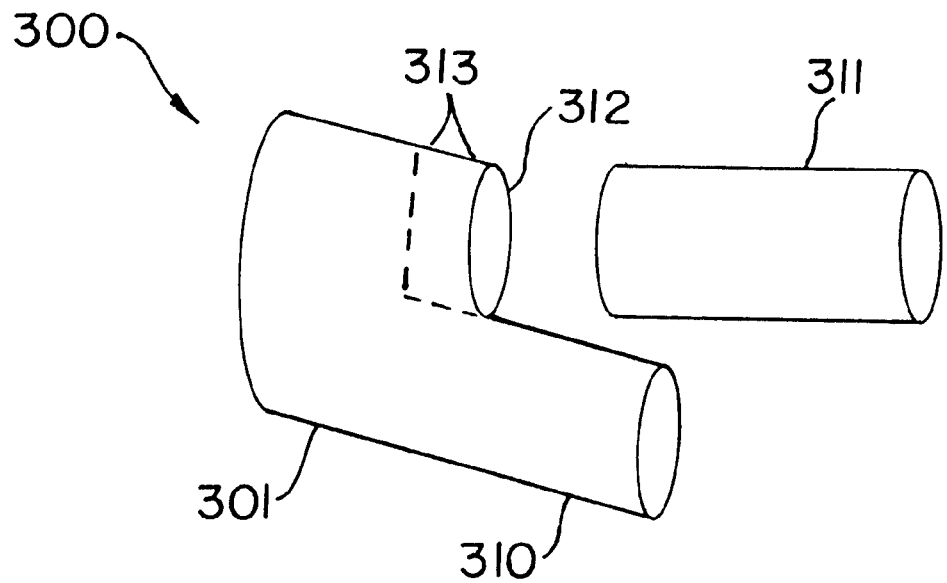
FIGS. 4B–4C illustrate a second coated bifurcated stent, in accordance with an embodiment of the present invention.
Figure 4C:
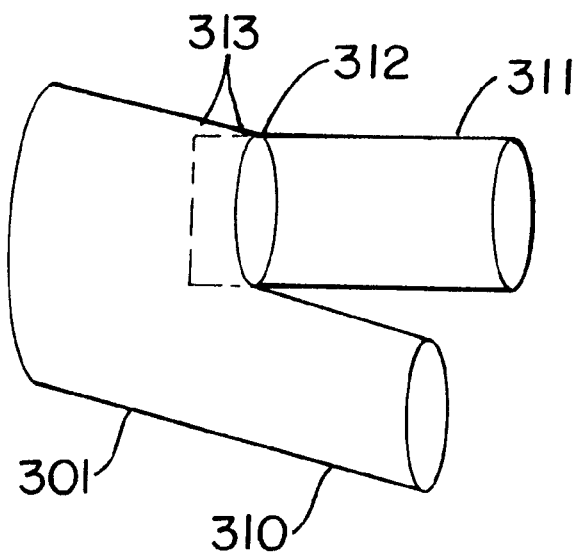

Alternatively, branch leg 311 may be selectively inserted into branch aperture 312 of tubular member 301 so that tubular member 301 and trunk leg 310 are separately delivered into a bifurcated lumen. In this case, tubular member 301 is provided with a branch aperture 312 as shown in FIG. 4B. When tubular member 301 is delivered to a bifurcated lumen, branch aperture 312 is aligned with the corresponding branch lumen. Tubular member portion 301 of stent 300 is thereafter expanded to secure its position in the lumen to be treated, and branch leg 311 is delivered through branch aperture 312 so that part of branch leg 311 is positioned into the branch lumen. Branch leg 311 is thereafter expanded as shown in FIG. 4C in an amount sufficient for its external surface to engage the portion of the tubular member 301 defining the branch aperture 312 and secure the branch leg 311 in the branch lumen and tubular member portion 301. In this embodiment of the invention, a region 313 surrounding branch aperture 312 includes both first and second coatings 102, 202 such that region 313 is most visible during fluoroscopy. In other words, the cross-sectional view of the struts 110 of stent. 300 appear as shown in FIG. 3B for region 313, and as shown in FIG. 3C elsewhere. Such a configuration is useful for aligning branch aperture 312 with a branch lumen so that branch leg 310 is thereafter easily inserted into the branch lumen.

The present invention provides stents having optimal radiopacity without sacrificing stent properties or performance. Those with skill in the art may recognize various modifications to the embodiments of the invention described and illustrated herein. Such modifications are meant to be covered by the spirit and scope of the appended claims.

What is claimed is:

1. A stent for deploying within a body lumen, said stent comprising:

a tubular member comprising struts which comprise a first material, said tubular member having a proximal end and a distal end and a longitudinal bore therethrough;

a first coating on said tubular member, said first coating substantially covering said tubular member and being substantially uniform in thickness, said first coating comprising a second material; and a second coating disposed between said tubular member and said first coating, said second coating covering only a portion of said tubular member;

wherein said second material is more radiopaque than said first material, and said second material is selected from the group consisting of gold, platinum, silver and tantalum.

2. The stent of claim 1, wherein said second coating is located at said proximal or said distal end of said tubular member.

3. The stent of claim 1, wherein when the stent is observed with fluoroscopy, said stent appears darker at the portion where said second coating exists than where said second coating does not exist.

4. The stent of claim 1, wherein the thickness of said second coating is approximately 1–20 percent of the thickness of an underlying strut.

5. The stent of claim 4, wherein the thickness of the second coating is approximately 5–15 percent of the thickness of an underlying strut.

6. The stent of claim 1, wherein said second coating is approximately 0.5–20 microns in thickness.

7. The stent of claim 6, wherein said second coating is approximately 5–15 microns in thickness.

8. The stent of claim 6, wherein said first coating is approximately 1 micron in thickness.

9. The stent of claim 1, wherein said second coating comprises a material selected from the group consisting of gold, platinum, silver and tantalum.

10. A stent for deploying within a body lumen, said stent comprising:

a tubular member comprising struts which comprise a first material, said tubular member having a proximal end and a distal end and a longitudinal bore therethrough, wherein said tubular member is bifurcated into a trunk leg and a branch leg for positioning in respective trunk and branch lumens of a bifurcated lumen;

a first coating on said tubular member, said first coating substantially covering said tubular member and being substantially uniform in thickness, said first coating comprising a second material; is wherein said second material is more radiopaque than said first material, and said second material is selected from the group consisting of gold, platinum, silver and tantalum said tubular member includes a branch aperture;

said branch leg may be selectively disposed within said tubular member; and a region of said tubular member adjacent to said branch aperture includes a second coating between said tubular member and said first coating.

11. A stent for deploying within a body lumen, said stent comprising:

a tubular member comprising struts which comprise a first material, said tubular member having a proximal end and a distal end and a longitudinal bore therethrough; and a first coating on said tubular member, said first coating substantially covering said tubular member and being substantially uniform in thickness, said first coating comprising a second material;

a second coating disposed between said tubular member and said first coating, said second coating covering only a portion of said tubular member, wherein said second material is more radiopaque than said first material.

12. The stent of claim 11, wherein said second coating is located at said proximal or said distal end of said tubular member.

13. The stent of claim 11, wherein the thickness of said second coating is approximately 1–20 percent of the thickness of an underlying strut.

* * * * *